US00PP25377P3

(12) United States Plant Patent
Kent

(10) Patent No.: US PP25,377 P3
(45) Date of Patent: Mar. 24, 2015

(54) ***GUZMANIA* PLANT NAMED 'KENT 33'**

(50) Latin Name: ***Guzmania* hybrid**
Varietal Denomination: Kent 33

(71) Applicant: Jeffrey Kent, Vista, CA (US)

(72) Inventor: Jeffrey Kent, Vista, CA (US)

( * ) Notice: Subject to any disclaimer, the term of this patent is extended or adjusted under 35 U.S.C. 154(b) by 0 days.

(21) Appl. No.: 13/986,278

(22) Filed: Apr. 18, 2013

(65) Prior Publication Data

US 2014/0317816 P1 Oct. 23, 2014

(51) Int. Cl.
*A01H 5/00* (2006.01)

(52) U.S. Cl.
USPC ..... Plt./371

(58) Field of Classification Search
CPC ..... A01H 5/00
USPC ..... Plt./371
See application file for complete search history.

(56) References Cited

PUBLICATIONS

Bromeliads in Australia, 2005.*

* cited by examiner

*Primary Examiner* — June Hwu
*Assistant Examiner* — Keith Robinson
(74) *Attorney, Agent, or Firm* — Cassandra Bright

(57) ABSTRACT

A new and distinct *Guzmania* cultivar named 'Kent 33' is disclosed, characterized by an inflorescence of unique coloration and configuration. The new variety is a *Guzmania*, normally used as an indoor ornamental plant.

1 Drawing Sheet

Latin name of the genus and species: *Guzmania* hybrid.
Variety denomination: 'Kent 33'.

BACKGROUND OF THE INVENTION

The new cultivar is a product of a chance discovery. The new variety originated as a chance, whole plant mutation from the, unpatented, variety *Guzmania* hybrid 'Marjan'. The new variety was discovered by the inventor, Jeffrey Kent Jul. 1, 1993 at a commercial greenhouse in Vista, Calif. belonging to the inventor.

Asexual reproduction of the new cultivar 'Kent 33' was first performed in Vista, Calif. by vegetative cuttings in the 1994. 'Kent 33' has since produced several generations by vegetative cuttings and has shown that the unique features of this cultivar are stable and reproduced true to type.

SUMMARY OF THE INVENTION

The cultivar 'Kent 33' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Kent 33' These characteristics in combination distinguish 'Kent 33' as a new and distinct *Guzmania* cultivar:

1. Short plant height.
2. Completely unique yellow and red striped inflorescence coloration.
3. Broad plant habit, with lower foliage angled nearly horizontal.
4. Narrow foliage with only slight arch.

PARENTAL COMPARISON

Plants of the new cultivar 'Kent 33' are similar to the parent variety 'Marjan' in most horticultural characteristics. However, 'Kent 33' differs from the parent in having a distinctive red stripe throughout the inflorescence whereas the parent has a solid yellow inflorescence. Additionally, the new variety is shorter than the parent.

COMMERCIAL COMPARISON

'Kent 33' can be compared to the commercial variety *Guzmania* 'Hilda', unpatented. Plants of 'Hilda' are similar to plants of 'Kent 33' in most horticultural characteristics, however, 'Kent 33' has an inflorescence with a distinctive red stripe, whereas 'Hilda' has a solid yellow inflorescence. Additionally, foliage of 'Kent 33' is somewhat narrower than that of 'Hilda'.

'Kent 33' can be compared to the unpatented commercial variety *Guzmania* 'Ostera'. Plants of 'Ostera' are similar to plants of 'Kent 33' in most horticultural characteristics, however, 'Kent 33' has an inflorescence with a distinctive red stripe, whereas 'Ostera' has an inflorescence which is orange, red and yellow, however in solid coloration, without striping. Additionally, the new variety is shorter than 'Ostera' and more suitable for 12 cm pot production.

BRIEF DESCRIPTION OF THE PHOTOGRAPH

The accompanying photograph in FIG. 1 illustrates in full color a typical plant of 'Kent 33' grown in a greenhouse in California. This plant is approximately 1 year old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Kent 33' plants grown in a climate controlled greenhouse in Vista, Calif. Temperatures ranged from 70° F. to 72° F. night and 80° F. to 87° F. day. No artificial light, photoperiodic treatments or chemical treatments were given to the plants. Measurements and numerical values represent averages of typical plant types.

Botanical classification: *Guzmania* hybrid 'Kent 33'.

Age of the plant described: Approximately 1 year from a vegetative cutting.

Container size of the plant described: 6 inch.

PLANT

Growth habit: Upright, arching, forming compact rosettes around a single axis. Single, straight, upright inflorescence arising from the center of plant.

Height: Approximately 32 cm in a 6 inch pot, measured from the soil level of the pot to top of inflorescence.

Plant spread: Approximately 56 cm in a 6 inch pot.

Normal pot size: 4", 6" pots.

Growth rate: Moderate.

Branching characteristics: Upright, non-branching.

Number of leaves per stem: Approximately 15.

Stem length: Approximately 16 cm.

Stem width: Approximately 3.6 cm.

Stem color: Near RHS Yellow-Green 144C with stripes near 144A.

Stem texture: Smooth.

Age of plant described: Approximately 1 year.

FOLIAGE

Leaf:

*Arrangement*.—Whorled, single occurring basal rosettes.

*Average length*.—Approximately 32 cm.

*Average width*.—Approximately 3.2 cm.

*Shape of blade*.—Ligulate.

*Aspect*.—Recurved.

*Apex*.—Acute.

*Base*.—Sheathing. Sheath length: Average 3.5 cm. Sheath width: Average 4.5 cm. Sheath color: Near RHS Yellow-Green 144C with stripes near 144A.

*Margin*.—Entire.

*Texture of top surface*.—Smooth, matte.

*Texture of bottom surface*.—Smooth, matte.

*Color*.—Young foliage upper side: Near RHS 137B. Young foliage under side: Near RHS 137C. Mature foliage upper side: Near RHS 139A. Mature foliage under side: Near RHS 137C.

*Venation*.—Type: Parallel. Venation coloration: Indistinguishable from foliage coloration.

Petiole: Not present, sessile.

INFLORESCENCE

General description: Simple spike(scape) consisting of many bracts only. Individual flowers are not distinguishable. Flower parts are highly compressed together. Spike emerges from the centre of the rosette. Inflorescence is formed by conspicuous bracts.

*Inflorescence height, excluding scape*.—Approximately 32 cm.

*Inflorescence width*.—Approximately 16.5 cm.

*Inflorescence lastingness*.—Approximately 10 weeks without any significant change in coloration.

Scape:

*Length*.—Approximately 14 cm.

*Width*.—Approximately 2.0 cm.

*Aspect*.—Very straight, Approximately 75° angle to rosette.

*Strength*.—Very strong.

*Color*.—Near RHS Yellow-green N144D with infrequent stripes near Red 44A

Bracts:

*Scape/lowermost bracts*.—Shape: Ligulate. Length: Approximately 8.5 cm, excluding sheath. Width: Approximately 3.0 cm. Quantity: Average 6. Tip: Acute. Base: Sheathed. Sheath length: Approximately 3.5 cm. Sheath width: Approximately 3.5 cm. Sheath color: Near RHS Yellow-Green 145C. Margin: Entire. Color Upperside: Margins near have a background color near RHS Greyed-Yellow 160A with faint stripes near 137C. Center of blade Yellow 11B with heavy stripes near Red 46C. Tip near Green 137A. Color Underside: Margins near have a background color near RHS Yellow 10C with faint stripes near 137C. Center of blade Yellow 11B with heavy stripes near Red 46C. Tip near Green 137C.

*Terminal bracts*.—Shape: Ligulate. Length: Approximately 6.5 cm, excluding sheath. Width: Approximately 3 cm. Quantity: Average 9. Tip: Acute. Base: Sheathed. Sheath length: Approximately 2 cm. Sheath width: Approximately 3.2 cm. Sheath color: Near RHS Yellow 9D with faint stripes near Red 46A. Margin: Entire. Coloration Terminal Bracts: Upperside: Background color near RHS Yellow 11 A stripes near Red 45B. Underside: Background color near RHS Yellow 11A stripes near Red 45B.

Individual flower and reproductive organs: Observed flowers are less than 5 mm in length and diameter, colored near Yellow-White 158C. Individual flower parts are indistinguishable and immeasurable, due to minute size.

OTHER CHARACTERISTICS

Disease resistance: Neither resistance nor susceptibility to diseases or pests has been observed in this variety.

Drought tolerance and cold tolerance: Observed to tolerate temperatures to 40° C. without any negative effects. Temperature tolerance above this range has not been observed. Tolerance of cold temperatures has not been observed.

Fruit/seed production: Not observed.

What is claimed is:

1. A new and distinct cultivar of *Guzmania* plant named 'Kent 33' as herein illustrated and described.

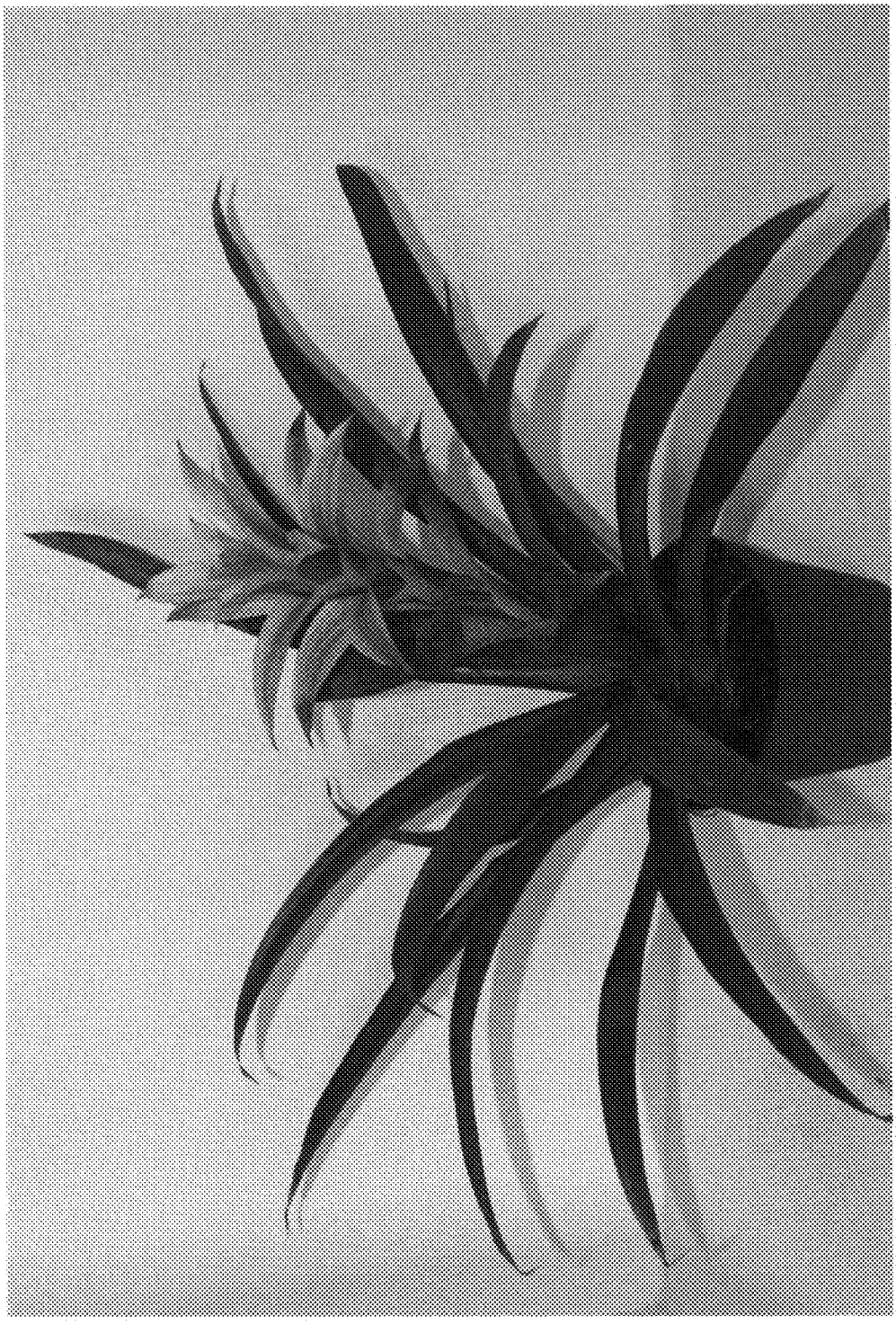

* * * * *